(12) United States Patent
Kim

(10) Patent No.: US 10,543,118 B2
(45) Date of Patent: Jan. 28, 2020

(54) JOINT DEVICE

(71) Applicants: SPHEREDYNE CO., LTD., Seoul (KR); Sug Whan Kim, Gimpo-si, Gyeonggi-do (KR)

(72) Inventor: Sug Whan Kim, Gimpo-si (KR)

(73) Assignees: SPHEREDYNE CO., LTD., Seoul (KR); Sug Whan Kim, Gyeonggi-Do (KR)

( * ) Notice: Subject to any disclaimer, the term of this patent is extended or adjusted under 35 U.S.C. 154(b) by 378 days.

(21) Appl. No.: 15/541,317

(22) PCT Filed: Jan. 4, 2016

(86) PCT No.: PCT/KR2016/000019
§ 371 (c)(1),
(2) Date: Jun. 30, 2017

(87) PCT Pub. No.: WO2016/108678
PCT Pub. Date: Jul. 7, 2016

(65) Prior Publication Data
US 2017/0367864 A1    Dec. 28, 2017

(30) Foreign Application Priority Data

Jan. 2, 2015    (KR) .................... 10-2015-0000285

(51) Int. Cl.
*A61F 5/01*    (2006.01)
*F16C 11/12*    (2006.01)

(52) U.S. Cl.
CPC ................ *A61F 5/01* (2013.01); *F16C 11/12* (2013.01); *A61F 5/013* (2013.01); *A61F 5/0123* (2013.01)

(58) Field of Classification Search
CPC ........ A61F 5/01; A61F 5/0106; A61F 5/0123; A61F 2/38; A61F 2/3886
See application file for complete search history.

(56) References Cited

U.S. PATENT DOCUMENTS 3,055,359 A * 9/1962 Palmer .................. A61F 5/0125
602/16
3,837,008 A * 9/1974 Bahler .................. A61F 2/4261
623/21.13

(Continued)

FOREIGN PATENT DOCUMENTS

KR    2020000001248 U    1/2000
KR    200378573 Y1    3/2005
(Continued)

OTHER PUBLICATIONS

International Search Report dated dated Apr. 29, 2016 of PCT Patent Application No. PCT/KR2016/000019.
(Continued)

*Primary Examiner* — Daniel J Wiley
(74) *Attorney, Agent, or Firm* — Nixon Peabody LLP; Jeffrey L. Costellia

(57) ABSTRACT

A joint apparatus includes a first fixed ring, a second fixed ring arranged spaced apart from the first fixed ring, an extension portion comprising a bar extending from the first fixed ring in a direction toward the second fixed ring and an end portion disposed at an end portion of the bar in the direction toward the second fixed ring, a first flexure extending from the second fixed ring in a direction toward the first fixed ring and supporting the end portion, and a second flexure extending from the second fixed ring in the direction toward the first fixed ring and supporting the end portion, the second flexure being disposed at an opposite side to the first flexure with respect to the extension portion.

20 Claims, 10 Drawing Sheets

(56) References Cited

U.S. PATENT DOCUMENTS

| | | | | |
|---|---|---|---|---|
| 4,256,097 A * | 3/1981 | Willis | A61F 5/0123 | 602/16 |
| 5,741,221 A * | 4/1998 | Wetz | A61F 5/0123 | 602/16 |
| 6,142,964 A * | 11/2000 | Gilmour | A61F 5/0125 | 602/16 |
| 6,488,711 B1 * | 12/2002 | Grafinger | A61F 2/3836 | 623/20.24 |
| 7,044,926 B2 * | 5/2006 | Carlson | A61F 5/0125 | 602/16 |
| 7,207,960 B2 * | 4/2007 | Kenney | A61F 5/0125 | 128/878 |
| 9,125,730 B2 * | 9/2015 | Ingimundarson | A61F 5/0123 | |
| 9,427,347 B2 * | 8/2016 | Pflaster | A61D 9/00 | |
| 2004/0002674 A1 * | 1/2004 | Sterling | A61F 5/0123 | 602/26 |
| 2004/0054311 A1 * | 3/2004 | Sterling | A61F 5/0123 | 602/26 |
| 2004/0068215 A1 * | 4/2004 | Adelson | A61F 5/0123 | 602/26 |
| 2006/0116616 A1 * | 6/2006 | Albrecht | A61F 5/0125 | 602/23 |
| 2008/0200856 A1 * | 8/2008 | Cadichon | A61F 5/0123 | 602/32 |
| 2014/0039367 A1 * | 2/2014 | Boraas | A61F 5/01 | 602/7 |
| 2014/0123440 A1 * | 5/2014 | Capra | A44B 11/25 | 24/163 R |

FOREIGN PATENT DOCUMENTS

| | | |
|---|---|---|
| KR | 100680655 B1 | 2/2007 |
| KR | 1020120078921 A | 7/2012 |
| KR | 101469539 B1 | 12/2014 |

OTHER PUBLICATIONS

Written Opinion dated Apr. 29, 2016 of PCT Patent Application No. PCT/KR2016/000019.

* cited by examiner

JOINT DEVICE

CROSS-REFERENCE TO RELATED APPLICATIONS

This application is the U.S. national phase of PCT International Patent Application No. PCT/KR2016/000019, filed Jan. 4, 2016, which claims the benefit of Korean Patent Application No. 10-2015-0000285, filed Jan. 2, 2015, the contents of which are incorporated by reference herein in their entirety.

TECHNICAL FIELD

The present inventive concept relates to a joint apparatus, and more particularly, to a joint apparatus which may increase a deformation degree of freedom in a preset direction

BACKGROUND ART

Joint apparatuses have been widely applied to animals, human bodies, mechanical apparatuses, or various industrial goods.

In general, the functions of joints are to provide: 1) a motion in a preset direction and a positional restoration, 2) a formation of one structure by one part and the other part in a combined state, and 3) a capability of being kept in one structure when no external force is applied, and separated when an external force over a particular strength is applied, and (4) a recombination to perform the original function once it is separated.

Although the joint apparatus should include the above functions, there is a limit that a general joint apparatus includes the above function (Korean Patent No. 1132806, Korean Patent Publication No. 2012-0020727)

DETAILED DESCRIPTION OF THE INVENTIVE CONCEPT

Technical Problem

The present inventive concept provides a joint apparatus which may increase a deformation degree of freedom in a preset direction

Technical Solution

According to an aspect of the present inventive concept, there is provided a joint apparatus includes a first fixed ring, a second fixed ring arranged spaced apart from the first fixed ring, an extension portion comprising a bar extending from the first fixed ring in a direction toward the second fixed ring and an end portion disposed at an end portion of the bar in the direction toward the second fixed ring, a first flexure extending from the second fixed ring in a direction toward the first fixed ring and supporting the end portion, and a second flexure extending from the second fixed ring in the direction toward the first fixed ring and supporting the end portion, the second flexure being disposed at an opposite side to the first flexure with respect to the extension portion.

The first flexure and the second flexure may be flexible.

A set of the extension portion, the first flexure, and the second flexure may be disposed at each of opposite sides with respect a center of the first fixed ring to correspond to each other.

The end portion may include a first surface and a second surface facing each other and a side surface connecting the first surface and the second surface, and the first flexure and the second flexure encompass a part of the side surface, a part of the first surface, and a part of the second surface.

The first flexure may include a first contact portion including a portion contacting the end portion and a first connection portion connecting the first contact portion and the second fixed ring, and the second flexure may include a second contact portion including a portion contacting the end portion and a second connection portion connecting the second contact portion and the second fixed ring.

The end portion may have a groove at an end portion facing the second fixed ring.

A point where the first contact portion and the first connection portion meet may be disposed to correspond to the groove of the end portion, and a point where the second contact portion and the second connection portion meet may be disposed to correspond to the groove of the end portion.

The end portion may include a first part having a first width that is a largest width, a second part having a second width and disposed in a direction toward the first fixed ring with respect to the first part, and a third part having a third width and disposed in the direction toward the second fixed ring with respect to the first part, in which the first contact portion encompasses the end portion from the third part to the second part via the first part.

The joint apparatus may further include a flexure connection portion that connects a point where the first contact portion and the first connection portion meet and a point where the second contact portion and the second connection portion meet, and supports the end portion.

The first flexure may include a first extended portion connected to the first contact portion to be disposed at an opposite side to the first connection portion with respect to the first contact portion, and the second flexure may include a second extended portion connected to the second contact portion to be disposed at an opposite side to the second connection portion with respect to the second contact portion.

The joint apparatus may further include a stopper that protrudes from the bar and limits a position of the second fixed ring in the direction toward the first fixed ring as a portion of the stopper in the direction toward the second fixed ring contacts the first extended portion or the second extended portion.

The joint apparatus may further include a stopper that protrudes from the bar and limits a position in the direction toward the first fixed ring of an end portion of the first flexure in the direction toward the first fixed ring, or a position in the direction toward the first fixed ring of an end portion of the second flexure in the direction toward the first fixed ring.

The joint apparatus may further include a third fixed ring disposed at an opposite side to the first fixed ring with respect to the second fixed ring, an additional extension portion comprising an additional bar extending from the second fixed ring in a direction toward the third fixed ring, and an additional end portion disposed at an end portion of the additional bar in the direction toward the third fixed ring, a first additional flexure extending from the third fixed ring in the direction toward the second fixed ring and supporting the additional end portion, and a second additional flexure extending from the third fixed ring in the direction toward the second fixed ring, supporting the additional end portion, and disposed at an opposite side to the first additional flexure with respect to the additional extension portion.

The joint apparatus may further include a plate disposed at an opposite side to the first fixed ring with respect to the second fixed ring, an additional extension portion comprising an additional bar extending from the second fixed ring in a direction toward the plate, and an additional end portion disposed at an end portion of the additional bar in a direction toward the plate, a first additional flexure extending from the plate in the direction toward the second fixed ring and supporting the additional end portion; and a second additional flexure extending from the plate in the direction toward the second fixed ring, supporting the additional end portion, and disposed at an opposite side to the first additional flexure with respect to the additional extension portion.

According to another aspect of the present inventive concept, there is provided a joint apparatus including a first fixed ring, a second fixed ring arranged spaced apart from the first fixed ring, an extension portion comprising a bar extending from the first fixed ring in the direction toward the second fixed ring and an end portion disposed at an end portion of the bar in the direction toward the second fixed ring, a first flexure extending from the second fixed ring in the direction toward the first fixed ring, a second flexure extending from the second fixed ring in the direction toward the first fixed ring, and a flexure connection portion connecting an end portion of the first flexure in the direction toward the first fixed ring and an end portion of the second flexure in the direction toward the first fixed ring.

The flexure connection portion may contact the end portion.

The flexure connection portion may encompass the end portion.

The end portion may include a first part having a first width that is a largest width and a second part having a second width and disposed in a direction toward the first fixed ring with respect to the first part, in which the flexure connection portion encompasses the first part and the second part of the end portion.

The flexure connection portion may have a concave shape in the direction toward the second fixed ring.

According to another aspect of the present inventive concept, there is provided a joint apparatus including a first fixed ring, a second fixed ring arranged spaced apart from the first fixed ring, an extension portion comprising a bar extending from the first fixed ring in the direction toward the second fixed ring and an end portion disposed at an end portion of the bar in the direction toward the second fixed ring, and a first flexure extending from the second fixed ring in the direction toward the first fixed ring, and comprising a first contact portion having a symmetric shape with respect to the bar and a portion contacting the end portion, and a first connection portion connecting the first contact portion and the second fixed ring.

The end portion may include a first part having a first width that is a largest width and a second part having a second width and disposed in a direction toward the first fixed ring with respect to the first part, in which the first contact portion encompasses the first part and the second part of the end portion.

Advantageous Effects

According to an embodiment of the present inventive concept, a joint apparatus may increase a deformation degree of freedom in a preset direction. However, the scope of the present inventive concept is not limited to the above effect.

BEST MODE

Figure 1:
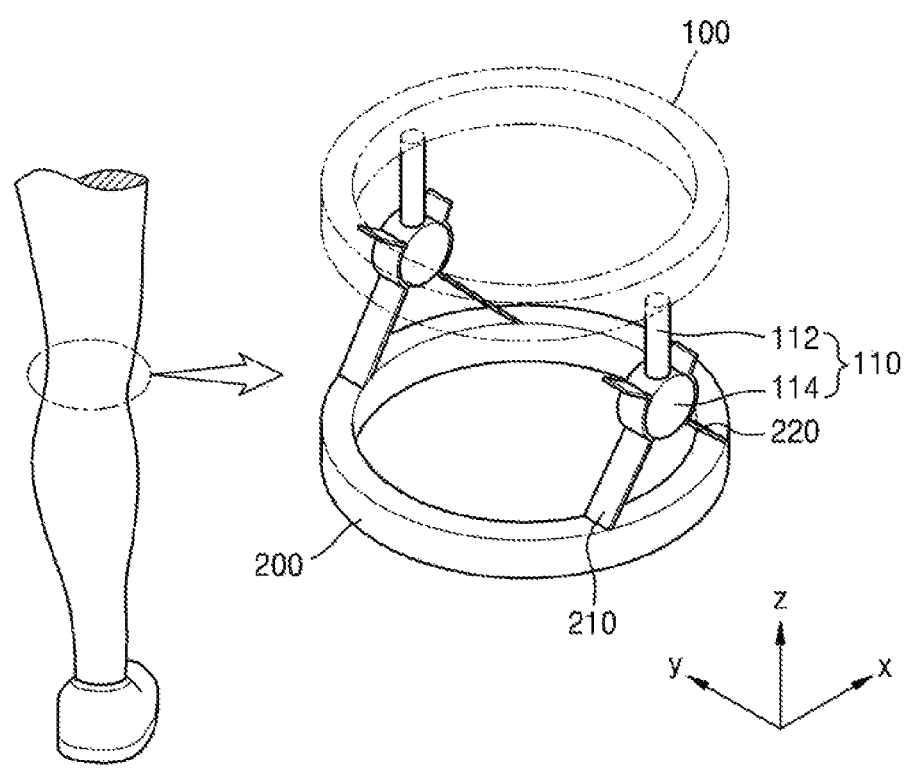
FIG. 1 is a perspective view schematically illustrating a joint apparatus according to an embodiment and a human body part to which the joint apparatus is applied.

Hereinafter, the present inventive concept will be described more fully with reference to the accompanying drawings, in which embodiments of the inventive concept are shown. This inventive concept may, however, be embodied in many different forms and should not be construed as limited to the embodiments set forth herein. Rather, these embodiments are provided so that this disclosure will be thorough and complete, and will fully convey the scope of the inventive concept to one of ordinary skill in the art. Sizes of components in the drawings may be exaggerated for convenience of explanation. In other words, since sizes and thicknesses, lengths, numbers, and shapes of components in the drawings are arbitrarily illustrated for convenience of explanation, the following embodiments are not limited thereto.

In the following embodiments, the x-axis, the y-axis and the z-axis are not limited to three axes of the rectangular coordinate system, and may be interpreted in a broader sense. For example, the x-axis, the y-axis, and the z-axis may be perpendicular to one another, or may represent different directions that are not perpendicular to one another. The direction indicated by a sign at the origin where the respective axes cross one another may denote a +direction of each axis.

It will be understood that when a component, such as a layer, a film, a region, or a plate, is referred to as being "on"

another component, the component can be directly on the other component or intervening components may be present thereon.

Figure 2:
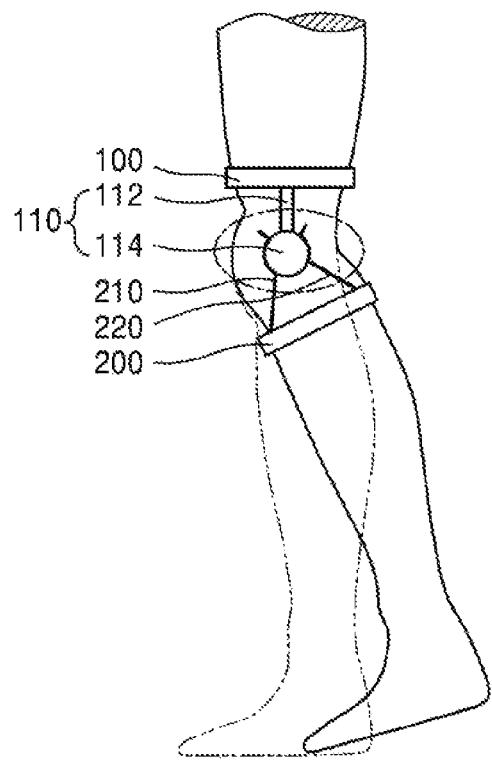
FIG. 2 is a side view schematically illustrating an example of using the joint apparatus of FIG. 1.
Figure 3:
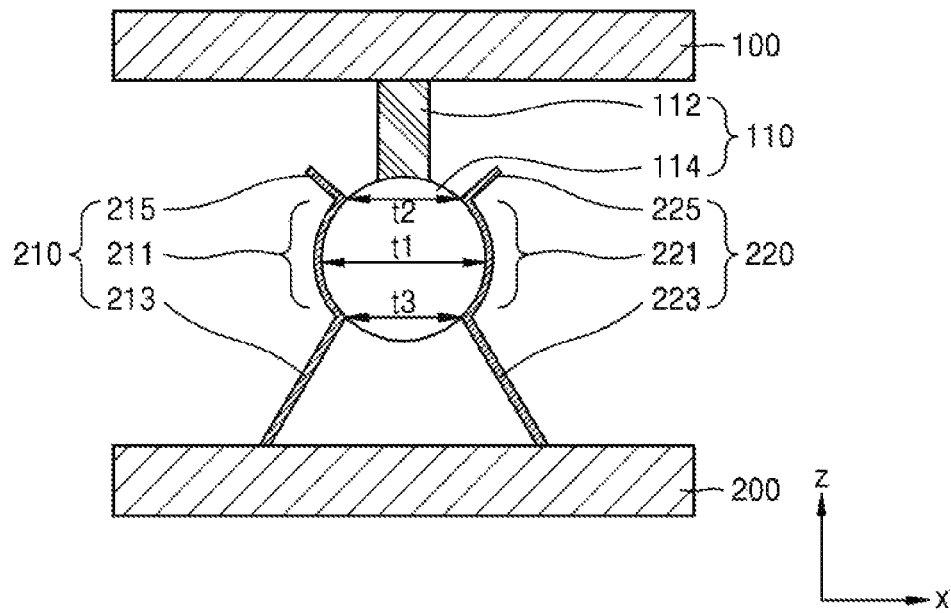
FIG. 3 is a side conceptual diagram schematically illustrating the joint apparatus of FIG. 1.

FIG. 1 is a perspective view schematically illustrating a joint apparatus according to an embodiment and a human body part to which the joint apparatus is applied. FIG. 2 is a side view schematically illustrating a state in which a user using the joint apparatus of FIG. 1 slightly bends his/her knee. FIG. 3 is a side conceptual diagram schematically illustrating the joint apparatus of FIG. 1. For reference, although FIG. 3 is not a sectional view, hatching is applied as a means to clearly express the relation between constituent elements. This is applied to other side conceptual diagrams illustrating embodiments that are described later.

The joint apparatus according to the present embodiment may include a first fixed ring 100, a second fixed ring 200, an extension portion 110, a first flexure 210, and a second flexure 220.

The first fixed ring 100 and the second fixed ring 200 are arranged spaced apart from each other, and may be respectively assembled to or disassembled from upper and lower portions (or front and back portions) of a joint of a human body, as illustrated in FIG. 2. For the assembly or disassembly, although it is not illustrated, each of the first fixed ring 100 and the second fixed ring 200 may have an opening portion and a locking device to be assembled or disassembled with respect to the human body. For example, each of the first fixed ring 100 and the second fixed ring 200 is formed by connecting two semicircular rings by using a hinge, and the locking device for combining the two semicircular rings may be provided at a position opposite to a portion where the hinge is located.

The extension portion 110 may have a bar 112 and an end portion 114. The bar 112 extends from the first fixed ring 100 in a direction toward the second fixed ring 200. The end portion 114 is located at an end portion of the bar 112 in the direction toward the second fixed ring 200. The bar 112 may have a cylindrical shape as illustrated in FIG. 1. The shape of the bar 112 is not limited thereto, and the bar 112 may have a shape of a column having a circular, oval, or polygonal section. The end portion 114 may have a variety of shapes, for example, a shape similar to a disc or a circular column as illustrated in FIG. 1. In FIG. 1, the end portion 114 is illustrated to be a disc or a circular column having a center axis in a y-axis direction. The shape of the end portion 114 is not limited thereto, and the end portion 114 may have a ball shape. The end portion 114 may have a variety of shapes having a section that is a circle, an oval, a polygonal surface, or a combination thereof.

Although FIG. 3 illustrates that the bar 112 is directly attached to the first fixed ring 100, the present disclosure is not limited thereto. For example, an elastic body such as a spring may be provided between the bar 112 and the first fixed ring 100. Alternatively, the bar 112 may be formed of a material having elasticity. In the present embodiment and embodiments or modified examples that are described later, the extension portion 110 may have a structure or a material having strength and elasticity.

The first flexure 210 extends from the second fixed ring 200 in a direction toward the first fixed ring 100. The first flexure 210 supports the extension portion 110. In detail, the first flexure 210 supports the end portion 114 of the extension portion 110. The second flexure 220 extends from the second fixed ring 200 in the direction toward the first fixed ring 100. The second flexure 220 supports the extension portion 110. In detail, the second flexure 220 with the first flexure 210 supports the end portion 114 of the extension portion 110.

As such, the first flexure 210 and the second flexure 220 support the end portion 114 from opposite sides (+x direction and -x direction) with respect to the extension portion 110. In other words, the second flexure 220 may be located at a side opposite to the first flexure 210 with respect to the extension portion 110. In addition to supporting the end portion 114, the first flexure 210 and the second flexure 220 may prevent the end portion 114 from escaping in a direction away from the second fixed ring 200. To this end, a thickness t1 of the thickest portion of the end portion 114 may be greater than a minimum distance between the first flexure 210 and the second flexure 220.

The first flexure 210 may have a variety of shapes, for example, as illustrated in FIG. 3, a first contact portion 211, a first connection portion 213, and a first extended portion 215. The first contact portion 211 may contact the end portion 114. The first connection portion 213 connects the first contact portion 211 and the second fixed ring 200. The first extended portion 215 is connected to the first contact portion 211 to be located at a side opposite to the first connection portion 213 with respect to the first contact portion 211. In other words, the first extended portion 215 may be understood to be an end portion of the first flexure 210 in the direction toward the first fixed ring 100. In some cases, the first flexure 210 may not include the first extended portion 215, which is the same as in the below-described embodiments and modified examples. The first flexure 210 may have flexible properties. This is to facilitate an operation of the joint apparatus by an elastic restoration force as described later.

The second flexure 220 may have a variety of shapes and may include, for example, a second contact portion 221, a second connection portion 223, and a second extended portion 225, as illustrated in FIG. 3. The second contact portion 221 may contact the end portion 114. The second connection portion 223 connects the second contact portion 221 and the second fixed ring 200. The second extended portion 225 is connected to the second contact portion 221 to be located at a side opposite to the second connection portion 223 with respect to the second contact portion 221. In other words, the second extended portion 225 may be understood to be an end of the second flexure 220 in the direction toward the first fixed ring 100. In some cases, the second flexure 220 may not include the second extended portion 225. The second flexure 220 may have flexible properties. This is to facilitate an operation of the joint apparatus by an elastic restoration force as described later.

The present disclosure is not limited thereto, and it is sufficient that the first flexure 210 is a flexible plate structure and has functions of the first contact portion 211, the first connection portion 213, and the first extended portion 215, due to at least one of bending, curving, and twisting, which is the same as in the below-described embodiments and modified examples and in the case of the second flexure 220.

As illustrated in FIGS. 1 and 2, the extension portion 110 may be located at opposite sides (+y direction and -y direction) with respect to the center of the first fixed ring 100 to correspond to each other, and likewise, each of the first flexure 210 and the second flexure 220 may be located at opposite sides (+y direction and -y direction) with respect to the center of the first fixed ring 100 to correspond to each other. In other words, a set of the extension portion 110, the first flexure 210 and the second flexure 220 may be located at opposite sides (+y direction and -y direction) with respect to the center of the first fixed ring 100 to correspond to each other. In this case, the joint apparatus of FIG. 1 may easily move in a preset direction. For example, in the case of the joint apparatus of FIG. 1, assuming that the position of the first fixed ring 100 is fixed and a z-axis passes through the center of the first fixed ring 100, the center of the second fixed ring 200 may move along a trajectory of a simple pendulum motion in a z-x plane. As such, in the case of the joint apparatus according to the present embodiment, as in a knee joint or a finger joint of a human body, a function of facilitating a motion in a preset direction while limiting a motion in other directions may be implemented.

Although FIGS. 1 to 3 illustrate that the first fixed ring 100 and the second fixed ring 200 have a uniform thickness, the present disclosure is not limited thereto. For example, the first fixed ring 100 may have a thin portion and the extension portion 110 may be located at the thin portion. Since the thin portion is relatively thinner that the other portion of the first fixed ring 100, the thin portion may have relatively flexible properties. When an external load or shock is applied to the joint apparatus in use, the thin portion may effectively absorb the load or shock, which is the same as in the below-described embodiments and modified examples.

The joint apparatus may be formed of metal and/or synthetic resin, but the present disclosure is not limited thereto. In other words, the joint apparatus may be formed of all types of materials having strength, elasticity, or flexibility solely or in a combination so that the strength, elasticity, or flexibility of an individual constituent element may be adjusted as necessary, which is the same as in the below-described embodiments and modified examples.

Although FIGS. 1 and 2 illustrate that, when the joint apparatus is in use, the first fixed ring 100 is located in a relatively upper side (+z direction) and the second fixed ring 200 is located in a relatively lower side (−z direction), the present disclosure is not limited thereto. For example, reversely, the joint apparatus may be used by locating the second fixed ring 200 in a relatively upper side (+z direction) and the first fixed ring 100 in a relatively lower side (−z direction). This may be understood to be a structure in which, for example, when the first fixed ring 100 is located in a relatively upper side (+z direction) and the second fixed ring 200 is located in a relatively lower side (−z direction), as illustrated in FIGS. 1 and 2, the bar 112 is located at the second fixed ring 200 and extends in a direction toward the first fixed ring 100, the end portion 114 is located at an end of the bar 112 in a direction toward the first fixed ring 100, the first flexure 210 and the second flexure 220 are located at the first fixed ring 100 and extend in the direction toward the second fixed ring 200, and the first flexure 210 and the second flexure 220 support the end portion 114.

All constituent elements of the joint apparatus according to the present embodiment may have strength and elasticity. In particular, the first flexure 210 and the second flexure 220 among the constituent elements may have more elasticity than the other constituent elements.

An example of an operation of the joint apparatus according to the present embodiment worn on a user is described below with reference to FIGS. 1 to 3. FIG. 1 illustrates that the user wearing the joint apparatus according to the present embodiment stands upright. The end portion 114 of the extension portion 110 is gripped by the first flexure 210 and the second flexure 220. Either the first flexure 210 or the second flexure 220 may be slightly bent, unlike the illustration of FIG. 3, to elastically grip the end portion 114.

When the user bends the knee as illustrated in FIG. 2, the second fixed ring 200 move in the +x and +z directions and the first flexure 210 and the second flexure 220 are deformed, for example, moved or bent. For example, as a point where the second contact portion 221 and the second extended portion 225 of the second flexure 220 meet contacts the bar 112, the second flexure 220 may be deformed, for example, bent. In this state, the second flexure 220 exerts an elastic restoration force to move the second fixed ring 200 to the original position. The elastic restoration force may help the user who needs to keep a knee part to maintain an upright state, easily unfold the knee. When the knee is bent by an external force that is not intended by the user, as illustrated in FIG. 2, the elastic restoration force may help the bent knee restored to the upright state as illustrated in FIG. 1.

As illustrated in FIGS. 1 to 3, the end portion 114 may have a first part having a first width t1 that is the largest width, a second part having a second width t2 located in a direction toward the first fixed ring 100 with respect to the first part, and a third part having a third width t3 located in the direction toward the second fixed ring 200 with respect to the first part. The first contact portion 211 may encompass the end portion 114 from the third part to the second part via the first part. The second contact portion 221 may also encompass the end portion 114 from the third part to the second part via the first part. Accordingly, the end portion 114 may be prevented from escaping between the first flexure 210 and the second flexure 220 in the direction away from the second fixed ring 200. The structure may also prevent the end portion 114 from escaping between the first flexure 210 and the second flexure 220 in a direction close to the second fixed ring 200.

Mode of the Inventive Concept

Figure 4:
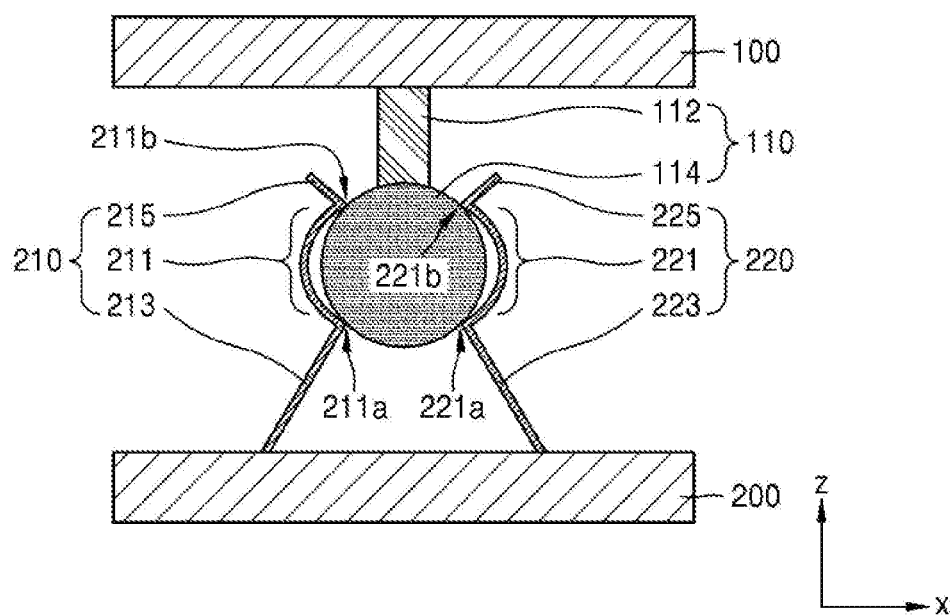
FIG. 4 is a side conceptual diagram schematically illustrating a joint apparatus according another embodiment.

Although FIG. 3 illustrates that the first contact portion 211 and the second contact portion 221 are in contact with the end portion 114 throughout the entire area thereof, the present disclosure is not limited thereto. For example, as illustrated in FIG. 4 that is a side conceptual diagram schematically illustrating a joint apparatus according another embodiment, it is sufficient that the first contact portion 211 contacts the end portion 114 at least one point, and that the second contact portion 221 also contacts the end portion 114 at least one point.

For example, each of the first contact portion 211 and the second contact portion 221 may contact the end portion 114 at two points. In detail, the first contact portion 211 may contact the end portion 114 at two points: a first point 211a where the first contact portion 211 and the first connection portion 213 meet, and a second point 211b where the first contact portion 211 and the first extended portion 215 meet. In other words, a portion between the first point 211a and the second point 211b of the first contact portion 211 may not be in contact with the end portion 114. The second contact portion 221 may also contact the end portion 114 at two points: a third point 221a where the second contact portion 221 and the second connection portion 223 meet, and a fourth point 221b where the second contact portion 221 and the second extended portion 225 meet. In other words, a portion between the third point 221a and the fourth point 221b of the second contact portion 221 may not be in contact with the end portion 114.

The contact method of the first contact portion 211 or the second contact portion 221 with the end portion 114 may not always be fixed. For example, as illustrated in FIG. 1, when a user stand upright wearing the joint apparatus according to the present embodiment, as illustrated in FIG. 3, the first contact portion 211 and the second contact portion 221 may be in contact with the end portion 114 throughout the entire area thereof.

Figure 5:
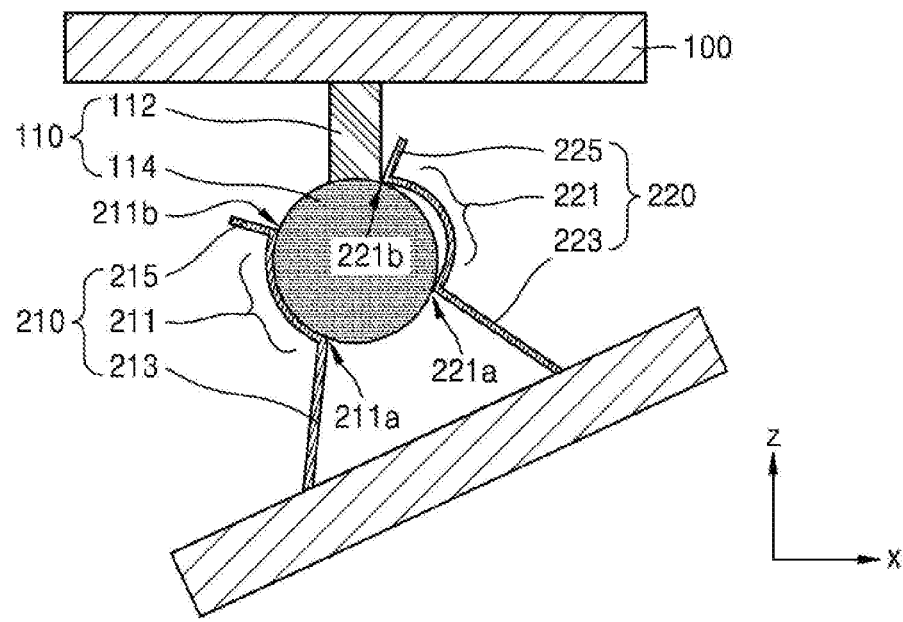
FIG. 5 is a side conceptual diagram schematically illustrating an example of using a joint apparatus according another embodiment.

In this state, when the user may take a motion of bending the knee as illustrated in FIG. 2, the second fixed ring 200 is moved in the +x and +z directions, and the second flexure 220 may be moved or deformed, for example, bent. In detail, as illustrated in FIG. 5, the first contact portion 211 is still in contact with the end portion 114 in the entire area thereof, and the second contact portion 221 is deformed such that the second contact portion 221 may contact the end portion 114 in a pressing state only at the two points: the third point 221a where the second contact portion 221 and the second connection portion 223 meet, and the fourth point 221b where the second contact portion 221 and the second extended portion 225 meet. In other words, the portion between the third point 221a and the fourth point 221b of the second contact portion 221 may not in contact with the end portion 114.

This is because, as the user takes a motion of bending the knee as illustrated in FIG. 2 and the second fixed ring 200 is moved in the +x and +z directions, the fourth point 221b where the second contact portion 221 and the second extended portion 225 meet contacts the bar 112 around a boundary between the bar 112 and the end portion 114, and thus the motion of the fourth point 221b is physically limited. In this state, the second flexure 220 having a deformed shape may exert an elastic restoration force to move the second fixed ring 200 to the original position, and the elastic restoration force may help the user who needs to maintain the knee portion in an upright state, not bend the knee. Furthermore, when the knee is bent by an external force that is not intended by the user, as illustrated in FIGS. 2 and 5, the elastic restoration force may help the bent knee restored to the original state that is an upright state as illustrated in FIGS. 1 and 3.

Figure 6:
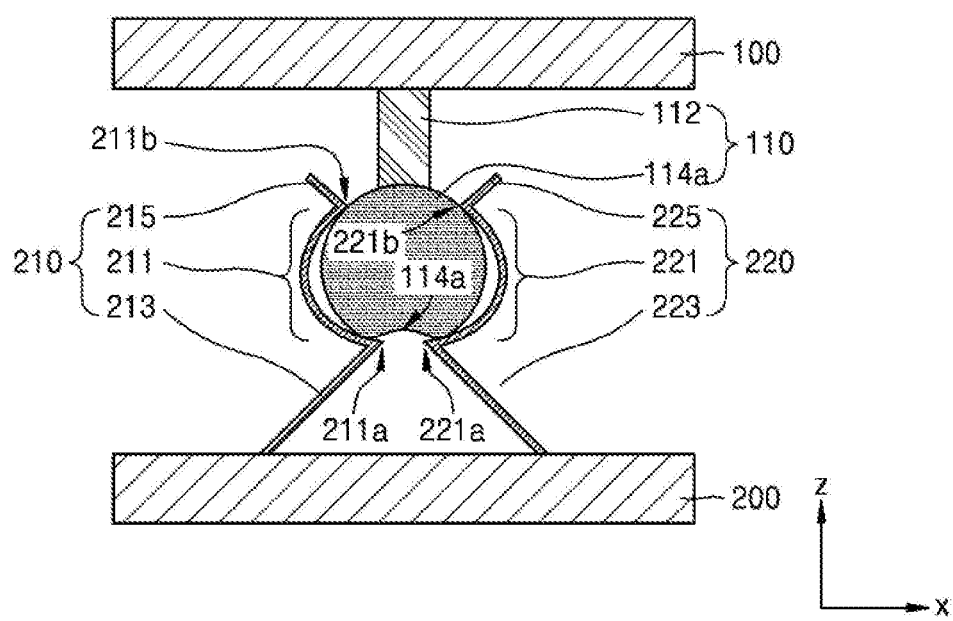
FIG. 6 is a side conceptual diagram schematically illustrating a joint apparatus according another embodiment.

FIG. 6 is a side conceptual diagram schematically illustrating a joint apparatus according another embodiment. As illustrated in FIG. 6, in the joint apparatus according to the present embodiment, the end portion 114 has a groove 114a at an end thereof in the direction toward the second fixed ring 200. The first point 211a where the first contact portion 211 and the first connection portion 213 meet is located corresponding to the groove 114a of the end portion 114, and the third point 221a where the second contact portion 221 and the second connection portion 223 meet is located corresponding to the groove 114a of the end portion 114. The first point 211a and the third point 221a are arranged spaced apart from each other, not contacting each other. In this state, the second point 211b where the first contact portion 211 and the first extended portion 215 meet may be in contact with the end portion 114, and the fourth point 221b where the second contact portion 221 and the second extended portion 225 meet may be in contact with the end portion 114.

In such a state, for example, when an excessive external force is applied to the first fixed ring 100 of the joint apparatus in the −z direction, the first fixed ring 100 may be moved in the direction toward the second fixed ring 200. Accordingly, there is a demand to prevent the end portion 114 from escaping between the first contact portion 211 and the second contact portion 221 in a direction close to the second fixed ring 200.

Figure 7:
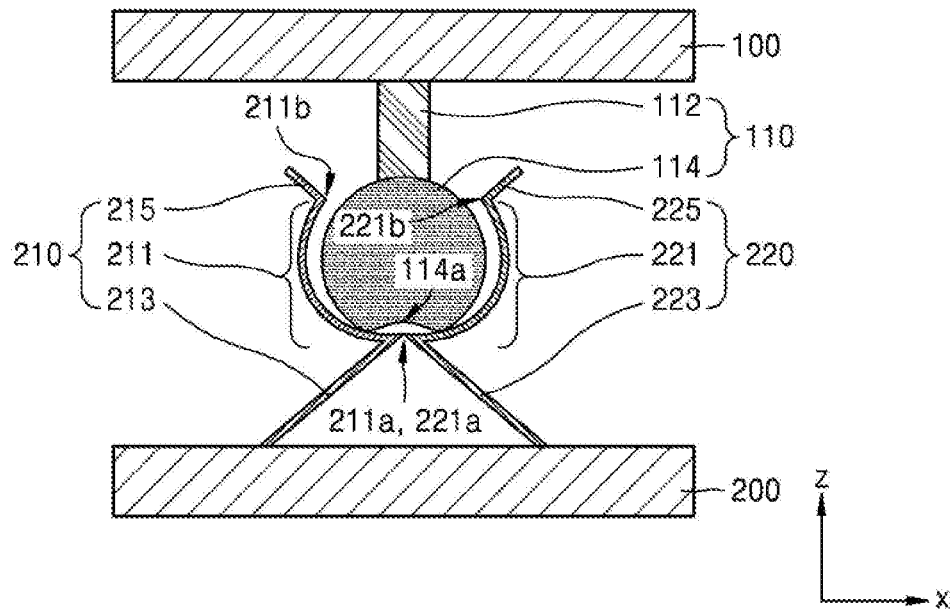
FIG. 7 is a side conceptual diagram schematically illustrating an example of using the joint apparatus of FIG. 6.

In the joint apparatus according to the present embodiment, as described above, the end portion 114 has the groove 114a at an end thereof in the direction toward the second fixed ring 200, and the first point 211a of the first contact portion 211 and the third point 221a of the second contact portion 221 are located corresponding to the groove 114a of the end portion 114. Accordingly, when an excessive external force is applied in such as state to the first fixed ring 100 and thus the first fixed ring 100 is moved in the direction toward the second fixed ring 200, as illustrated in FIG. 7 that is a side conceptual diagram schematically illustrating an example of using the joint apparatus of FIG. 6, the first flexure 210 and the second flexure 220 is deformed by a force of the end portion 114 pressing the first flexure 210 and the second flexure 220, and thus the first point 211a and the third point 221a contact each other. In the process, the second point 211b where the first contact portion 211 and the first extended portion 215 meet may be spaced apart from the end portion 114, the fourth point 221b where the second contact portion 221 and the second extended portion 225 meet may also be spaced apart from the end portion 114.

As such, when the excessive external force is applied to the joint apparatus and thus the first fixed ring 100 is moved in the direction toward the second fixed ring 200, the first point 211a and the third point 221a contact each other. Accordingly, the escape of the end portion 114 between the first contact portion 211 and the second contact portion 221 in the direction toward the second fixed ring 200 may be effectively prevented. When the external force is removed, the first flexure 210 and the second flexure 220 may be returned to the original shape shown in FIG. 6 due to the flexible properties of the first flexure 210 and the second flexure 220.

Figure 8:
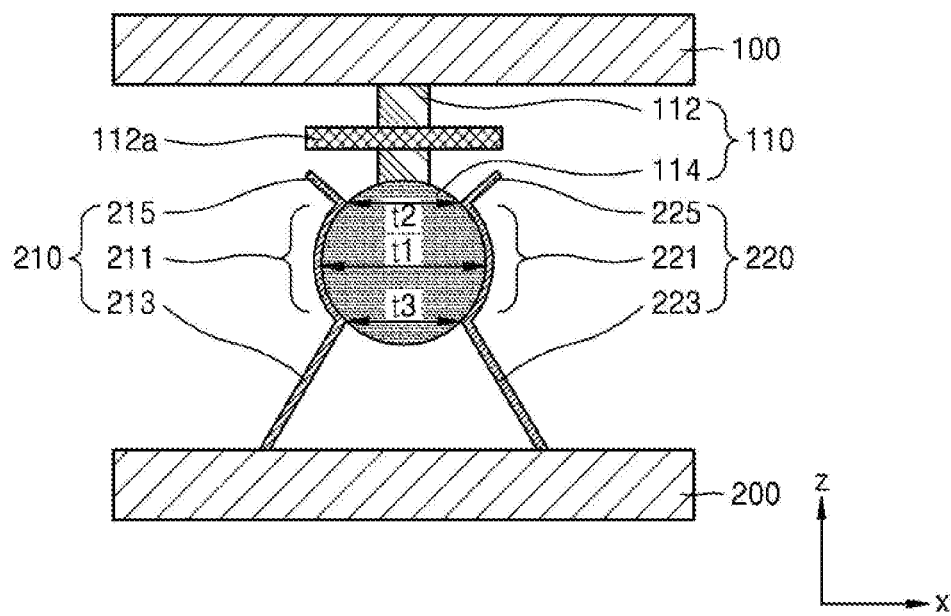
FIG. 8 is a side conceptual diagram schematically illustrating a joint apparatus according another embodiment.

FIG. 8 is a side conceptual diagram schematically illustrating a joint apparatus according another embodiment. The joint apparatus according to the present embodiment may further include a stopper 112a. The stopper 112a may protrude from the bar 112. The stopper 112a and the bar 112 may be integrally formed, or the stopper 112a that is a separate element may be attached to the bar 112. As a portion of the stopper 112a in the direction toward the second fixed ring 200 contacts the first extended portion 215 of the first flexure 210, the position of the second fixed ring 200 in the direction toward the first fixed ring 100 may be limited. The portion of the stopper 112a in the direction toward the second fixed ring 200 may contact the second extended portion 225 of the second flexure 220.

When the excessive external force is applied to the joint apparatus, the first fixed ring 100 may be moved in the direction toward the second fixed ring 200. In this state, the escape of the end portion 114 between the first contact portion 211 and the second contact portion 221 in the direction close to the second fixed ring 200 needs to be prevented. In the joint apparatus according to the present embodiment, when the excessive external force is applied to the joint apparatus, the portion of the stopper 112a in the direction toward the second fixed ring 200 may contact the first extended portion 215 of the first flexure 210 and the second extended portion 225 of the second flexure 220. Accordingly, the escape of the end portion 114 between the first contact portion 211 and the second contact portion 221 in the direction close to the second fixed ring 200 may be effectively prevented and also the joint apparatus may be effectively prevented from being damaged.

Although FIG. 8 illustrates that the first flexure 210 has the first extended portion 215 and the second flexure 220 has the second extended portion 225, the present disclosure is not limited thereto. For example, when the first flexure 210 does not have the first extended portion 215 and the second flexure 220 does not have the second extended portion 225, an end portion of the first contact portion 211 in the direction toward the first fixed ring 100 and an end portion of the second contact portion 221 in the direction toward the first fixed ring 100 may face the stopper 112a or may contact the stopper 112a, and thus a variety of modifications are possible. Accordingly, the position of an end portion of the first flexure 210 in the direction toward the first fixed ring 100 may be limited in the direction toward the first fixed ring 100 or the position of an end portion of the second flexure 220 in the direction toward the first fixed ring 100 may be limited in the toward the first fixed ring 100.

Figure 9:
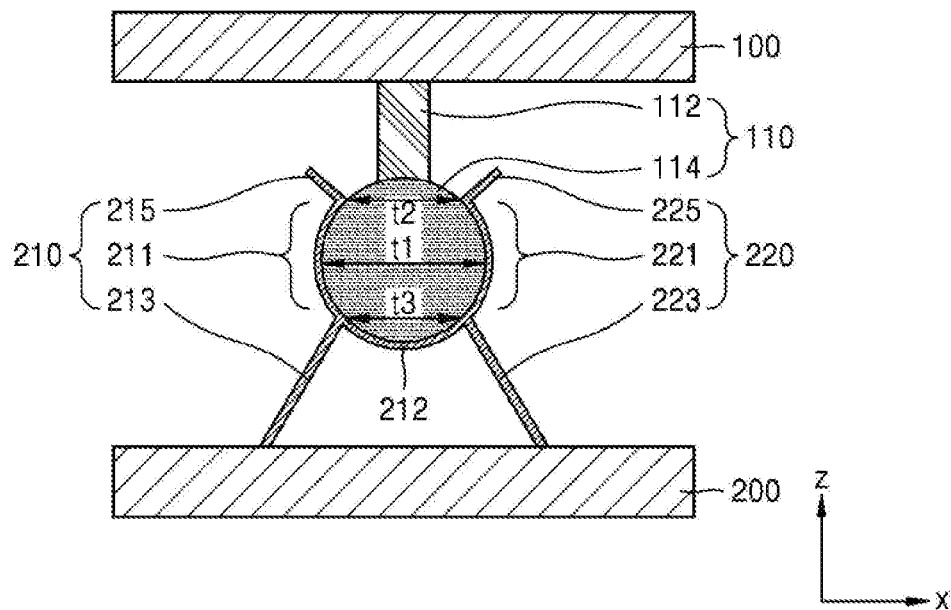
FIG. 9 is a side conceptual diagram schematically illustrating a joint apparatus according another embodiment.

FIG. 9 is a side conceptual diagram schematically illustrating a joint apparatus according another embodiment. The joint apparatus according to the present embodiment is different from the joint apparatus according to the above-described embodiment of FIG. 3 in that the joint apparatus according to the present embodiment further include a flexure connection portion 212. The flexure connection portion 212 may connect the first flexure 210 and the second flexure 220 as illustrated in FIG. 9. In detail, the flexure connection portion 212 may support the end portion 114 by connecting a point where the first contact portion 211 and the first connection portion 213 of the first flexure 210 meet and a point where the second contact portion 221 and the second connection portion 223 of the second flexure 220 meet. Accordingly, as the elasticity of the first flexure 210 and the second flexure 220, which are connected to each other, is reinforced due to the existence of the flexure connection portion 212, the escape of the end portion 114 between the first flexure 210 and the second flexure 220 in the direction away from the second fixed ring 200 may be prevented. Furthermore, the flexure connection portion 212 may function as a stopper to prevent the end portion 114 from moving in a direction close to the second fixed ring 200.

Figure 10:
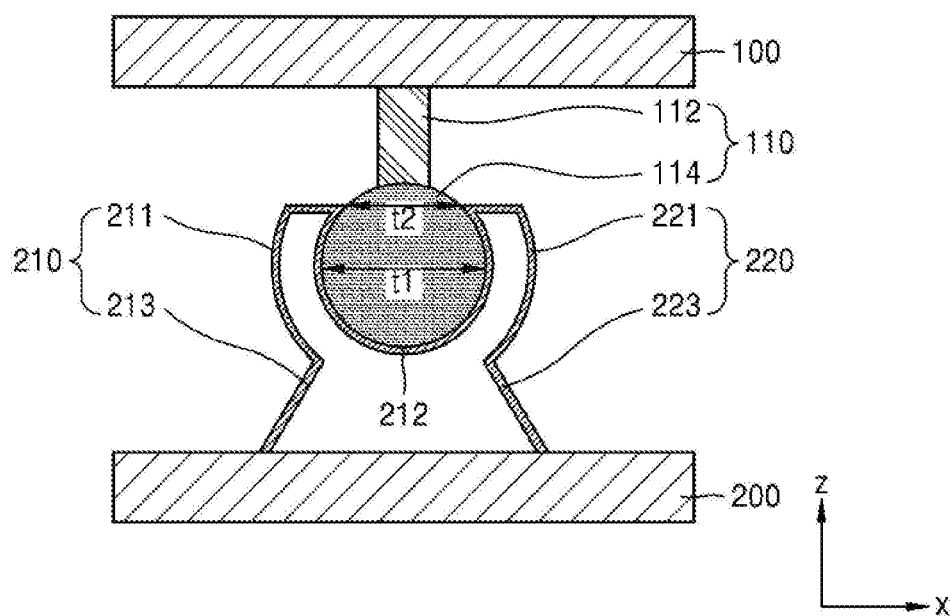
FIG. 10 is a side conceptual diagram schematically illustrating a joint apparatus according another embodiment.

FIG. 10 is a side conceptual diagram schematically illustrating a joint apparatus according another embodiment. As illustrated in FIG. 10, the first flexure 210 and the second flexure 220 extend from the second fixed ring 200 in the direction toward first fixed ring 100. The flexure connection portion 212 connects the first flexure 210 and the second flexure 220. In detail, the flexure connection portion 212 supports the end portion 114 by connecting the end portion of the first flexure 210 in the direction toward the first fixed ring 100 and the end portion of the second flexure 220 in the direction toward the first fixed ring 100. To this end, not the first flexure 210 or the second flexure 220, but the flexure connection portion 212 may contact the end portion 114. Furthermore, the flexure connection portion 212 may encompass the end portion 114. Accordingly, the flexure connection portion 212 may have a concave shape in the direction toward the second fixed ring 200 (−z direction).

According to the above structure, the end portion 114 is stably encompassed and supported by the flexure connection portion 212, and the reinforced elasticity may prevent the end portion 114 from escaping between the first flexure 210 and the second flexure 220 in the direction away from the second fixed ring 200. Furthermore, the flexure connection portion 212 may have a stopper function to prevent the end portion 114 from moving in the direction close to the second fixed ring 200. Also, there is a demand to prevent the end portion 114 from escaping from the flexure connection portion 212. To this end, when the end portion 114 has the first part having the first width t1 that is the largest width and the second part having the second width t2 located in the direction toward the first fixed ring 100 with respect to the first part, the flexure connection portion 212 may encompass not only the end portion of the end portion 114 in the direction toward the second fixed ring 200, but also the first part and the second part of the end portion 114.

Figure 11:
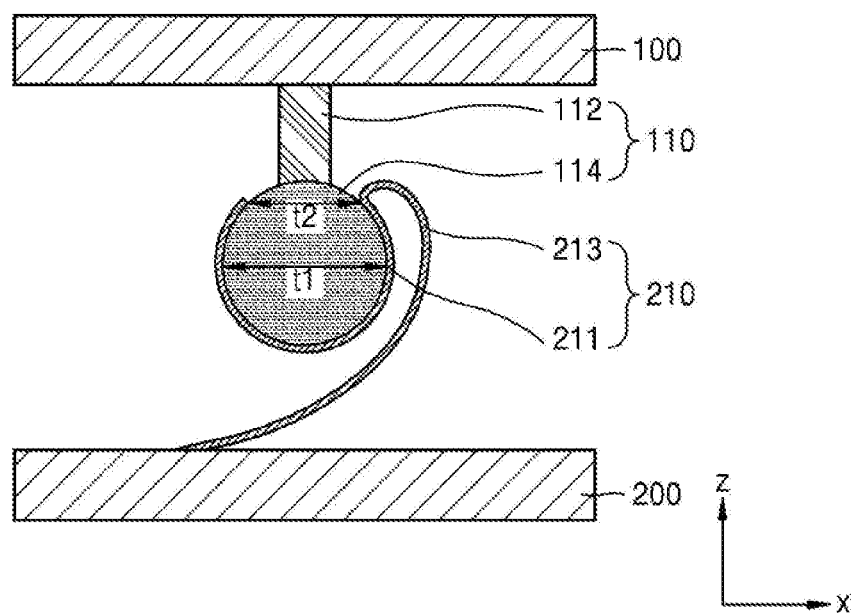
FIG. 11 is a side conceptual diagram schematically illustrating a joint apparatus according another embodiment.

Although the above-described embodiments relate to a case in which the joint apparatus such as an artificial joint includes the first flexure 210 and the second flexure 220, the present disclosure is not limited thereto. For example, as illustrated in FIG. 11 that is a side conceptual diagram schematically illustrating a joint apparatus according another embodiment, the joint apparatus may include the first flexure 210 only. In this case, in order for the first flexure 210 to stably support the end portion 114, the first contact portion 211 may have a shape that is symmetrical with respect to the bar 112 of the extension portion 110. In detail, the end portion 114 has the first part having the first width t1 that is the largest width and the second part having the second width t2 located in the direction toward the first fixed ring 100 with respect to the first part, the first contact portion 211 that is symmetrical to the bar 112 may encompass the first part and the second part of the end portion 114. The first connection portion 213 connects the first contact portion 211 and the second fixed ring 200.

Figure 12:
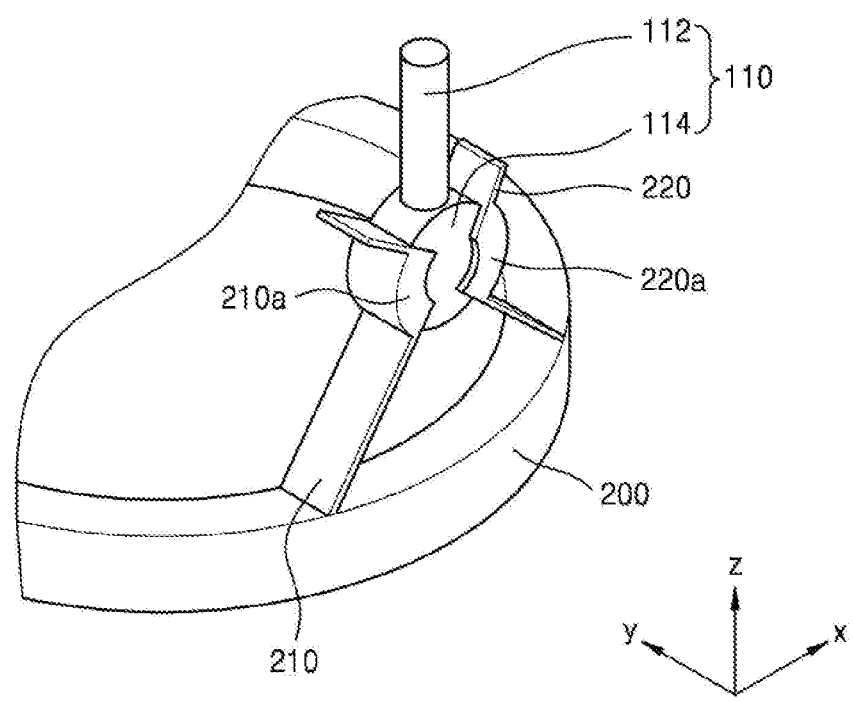
FIG. 12 is a perspective view schematically illustrating a joint apparatus according another embodiment.

FIG. 12 is a perspective view schematically illustrating a joint apparatus according another embodiment. A difference between the joint apparatus according to the present embodiment and the joint apparatus described with reference to FIG. 3 lies in that the first flexure 210 and the second flexure 220 more stably support the end portion 114.

In detail, as illustrated in FIG. 12, the end portion 114 may include a first surface and a second surface facing each other and a side surface connecting the first surface and the second surface. For example, as illustrated in FIG. 12, the end portion 114 may have a shape similar to a disc or a low-profile circular cylinder. The first flexure 210 may have a first flange portion 210a encompassing a part of a side surface of the end portion 114. The second flexure 220 may also have a second flange portion 220a encompassing a part of the side surface of the end portion 114. According to the above structure, as in the knee joint or the finger joint of a human body, a function of facilitating a motion in a preset direction while limiting a motion in other directions (like the −y direction or +y direction) may be more certainly implemented. The structure of the first flange portion 210a or the second flange portion 220a may be applied not only to the above-described embodiments, but also to embodiments to be described later or modified examples thereof.

Figure 13:
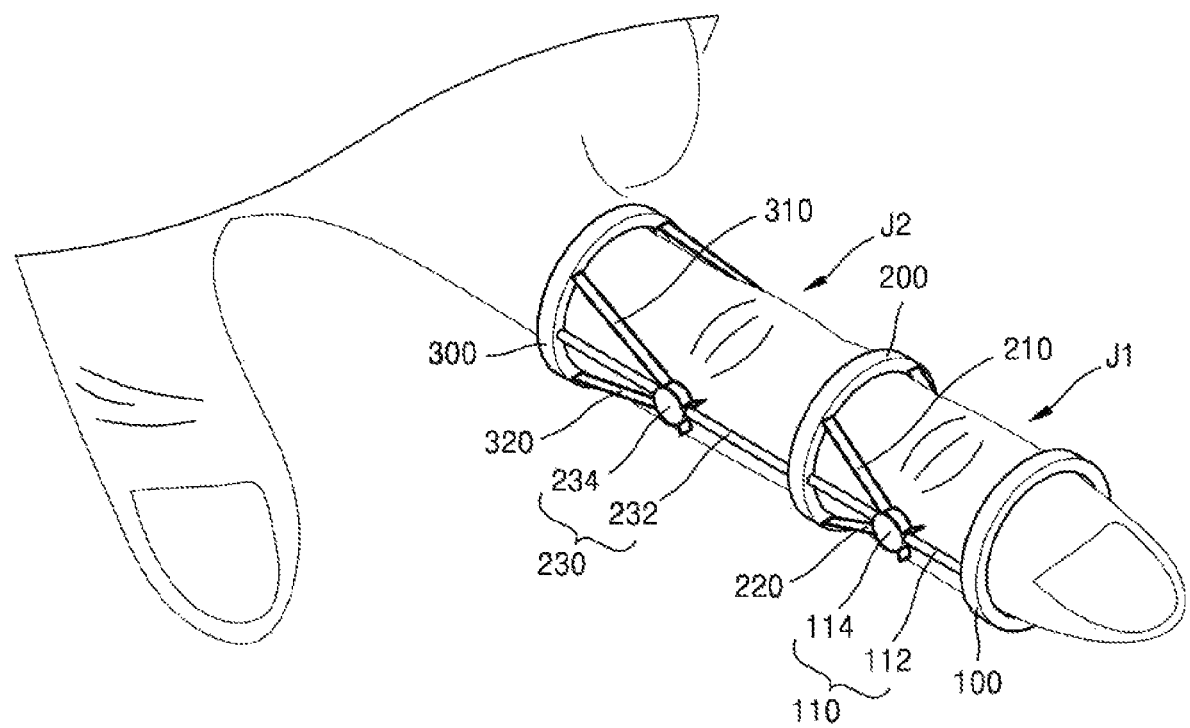
FIG. 13 is a perspective view schematically illustrating a joint apparatus according another embodiment, and an example of using the joint apparatus.

FIG. 13 is a perspective view illustrating a case in which the joint apparatus of FIGS. 1 to 3 is mounted on a finer of a human body.

As illustrated in FIG. 13, the first fixed ring 100 and the second fixed ring 200 are mounted on a finger with a first joint J1 at a fingertip portion. The first fixed ring 100 is mounted on the fingertip portion and the second fixed ring 200 is mounted between the first joint J1 at the fingertip portion and a second joint J2 in the middle of the finger. The extension portion 110 extends from the first fixed ring 100 in the direction toward the second fixed ring 200. The first flexure 210 and the second flexure 220 extend from the second fixed ring 200 in the direction toward the first fixed ring 100. The first contact portion 211 of the first flexure 210 and the second contact portion 221 of the second flexure 220 are engaged with the end portion 114 of the extension portion 110 around the first joint J1 at the fingertip portion. According to the above structure, the joint apparatus may facilitate a motion of a finger at the first joint J1.

Furthermore, the joint apparatus, as illustrated in FIG. 13, the extension portion 110, the first flexure 210, and the second flexure 220 are located at both sides of the first joint J1 of the finger, the finger may not be moved in a direction other than a typical movement direction of the first joint J1 at the first joint J1 of the finger. Accordingly, the joint apparatus may not only facilitate a motion in the typical movement direction at the first joint J1, but also protect the first joint J1.

The joint apparatus may include a third fixed ring 300, in addition to the first fixed ring 100 and the second fixed ring 200, as illustrated in FIG. 13. The third fixed ring 300 may be mounted on the finger such that the second joint J2 of the finger is located between the second fixed ring 200 and the third fixed ring 300.

An additional extension portion 230 extends from the second fixed ring 200 in a direction toward the third fixed ring 300. The additional extension portion 230 may include an additional bar 232 and an additional end portion 234. The additional extension portion 230 may have a structure similar to the extension portion 110. A first additional flexure 310 and a second additional flexure 320 extend from the third fixed ring 300 in the direction toward the second fixed ring 200. The first additional flexure 310 and the second additional flexure 320 may have structures similar to the first flexure 210 and the second flexure 220. The additional end portion 234 of the additional extension portion 230 contacts the first additional flexure 310 and the second additional flexure 320 around the second joint J2 in the middle of the finger. According to the above structure, the joint apparatus may facilitate a motion of the finger at the second joint J2 of the finger.

Furthermore, as the joint apparatus has the additional extension portion 230, the first additional flexure 310, and the second additional flexure 320 located at both sides of the second joint J2 of the finger, as illustrated in FIG. 13, the finger may not move in a direction other than the typical movement direction of the second joint J2 at the second joint J2 of the finger. Accordingly, the joint apparatus may facilitate a motion of the finger in the typical movement direction at the second joint J2, and may also protect the second joint J2.

Although FIG. 13 illustrates that the configuration and the connection structure of the extension portion 110 and the additional extension portion 230 are similar to those of the joint apparatus according to the above-described embodiment of FIGS. 1 to 3, the present disclosure is not limited thereto. For example, the joint apparatuses according to the above-described embodiments and modified examples thereof described with reference to FIGS. 4 to 12 may be located around the first joint J1 of the finger. Also, the joint apparatuses according to the above-described embodiments and modified examples thereof described with reference to FIGS. 4 to 12 may be located around the second joint J2 of the finger.

Figure 14:
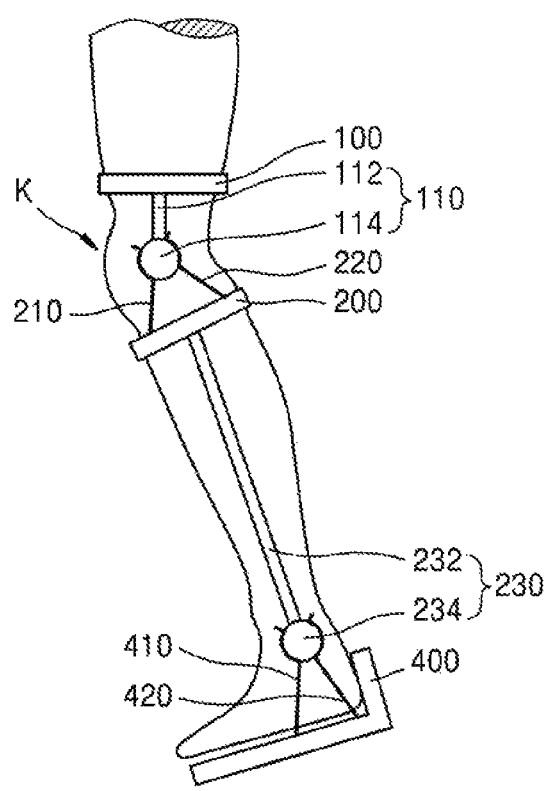
FIG. 14 is a side view schematically illustrating a joint apparatus according another embodiment, and an example of using the joint apparatus.

FIG. 14 is a side view schematically illustrating a joint apparatus according another embodiment, and an example of using the joint apparatus.

The joint apparatus according to the present embodiment, similarly to the joint apparatus of FIG. 1, may include a plate 400, the additional extension portion 230, a first additional flexure 410, and a second additional flexure 420, in addition to the first fixed ring 100, the second fixed ring 200, the extension portion 110, the first flexure 210, and the second flexure 220.

The first fixed ring 100 may be fixed to a thigh of the human body. The second fixed ring 200 may be fixed to a leg of the human body such that a knee joint K is located between the first fixed ring 100 and the second fixed ring 200. The plate 400 is located at the opposite side to the first fixed ring 100 with respect to the second fixed ring 200. The plate 400 may correspond to the shape of an insole or outsole of a typical shoe and a heel portion including a heel and an ankle. For example, the plate 400 may have a bent shape corresponding to the sole of a foot and the Achilles' tendon of the human body.

The additional extension portion 230 may include the additional bar 232 extending from the second fixed ring 200 in a direction toward the plate 400, and the additional end portion 234 located at an end of the additional bar 232 in the direction toward the plate 400. The first additional flexure 410 extends from the plate 400 in the direction toward the second fixed ring 200, and supports the additional end portion 234. The second additional flexure 420 extends from the plate 400 in the direction toward the second fixed ring 200, and supports the additional end portion 234.

In the joint apparatus according to the present embodiment, the first flexure 210 and the second flexure 220 are engaged with the end portion 114 of the extension portion 110 around the knee joint K. According to the above structure, the joint apparatus may not only support the knee joint K of a leg, but also facilitate a motion of the knee joint K. Furthermore, the first additional flexure 410 and the second additional flexure 420 are engaged with the additional end portion 234 of the additional extension portion 230 around an ankle joint. According to the above structure, the joint apparatus according to the present embodiment may not only support the ankle joint, but also facilitate a motion of the ankle joint.

Furthermore, in the joint apparatus, as illustrated in FIG. 14, as the extension portion 110, first flexure 210, and the second flexure 220 are located at both sides of the knee joint K, the knee joint K may not be moved in a direction other than the typical movement direction of the knee joint K. Accordingly, the joint apparatus may facilitate a motion of the knee joint K in the typical movement direction of the knee joint K, and may also protect the knee joint K.

Furthermore, as illustrated in FIG. 14, when the joint apparatus is in use, since the sole of a user's foot is spaced apart from the plate 400 without touching the plate 400, a load due to the weight of a human body may not be applied to the ankle and may be transmitted to other portion of a leg, that is, a knee or a thigh portion above the knee, via the first fixed ring 100 and the second fixed ring 200. Accordingly, when a patient who is injured in the ankle uses the joint apparatus according to the present embodiment, the patient may be able to walk without a load applied to an injured portion such as the ankle. The joint apparatus may further include a fixing device (not shown) for fixing the plate 400 and a user's foot.

Although FIG. 14 illustrates that the configuration and the connection of the extension portion 110, the first flexure 210, and the second flexure 220 are similar to those of the joint apparatus according to the above-described embodiment of FIGS. 1 to 3, the present disclosure is not limited thereto. For example, the joint apparatuses according to the above-described embodiments and modified examples thereof described with reference to FIGS. 4 to 12 may be located around the knee joint K. Also, the joint apparatuses according to the above-described embodiments and modified examples thereof described with reference to FIGS. 4 to 12 may be located around the ankle joint.

While the present inventive concept has been particularly shown and described with reference to preferred embodiments using specific terminologies, the embodiments and terminologies should be considered in descriptive sense only and not for purposes of limitation. Therefore, it will be understood by those of ordinary skill in the art that various changes in form and details may be made therein without departing from the spirit and scope of the present inventive concept as defined by the following claims.

INDUSTRIAL APPLICABILITY

According to the above-described embodiments, the joint apparatus that can increase a deformation degree of freedom in a preset direction may be implemented.

The invention claimed is:

1. A joint apparatus comprising:
a first fixed ring;
a second fixed ring arranged spaced apart from the first fixed ring;
an extension portion comprising a bar extending from the first fixed ring in a direction toward the second fixed ring and an end portion disposed at an end portion of the bar in the direction toward the second fixed ring;
a first flexure extending from the second fixed ring in a direction toward the first fixed ring and supporting the end portion; and
a second flexure extending from the second fixed ring in the direction toward the first fixed ring and supporting the end portion, the second flexure being disposed at an opposite side to the first flexure with respect to the extension portion;
wherein the first flexure comprises a first contact portion including a portion at least partially encompassing a first rounded part of the end portion and a first connection portion connecting the first contact portion and the second fixed ring, and the second flexure comprises a second contact portion including a portion at least partially encompassing a second rounded part of the end portion and a second connection portion connecting the second contact portion and the second fixed ring.

2. The joint apparatus of claim 1, wherein the first flexure and the second flexure are flexible.

3. The joint apparatus of claim 1, wherein a set of the extension portion, the first flexure, and the second flexure is disposed at each of opposite sides with respect to a center of the first fixed ring to correspond to each other.

4. The joint apparatus of claim 1, wherein the end portion comprises a first surface and a second surface facing each other and a side surface connecting the first surface and the second surface, and the first flexure and the second flexure encompass a part of the side surface, a part of the first surface, and a part of the second surface.

5. The joint apparatus of claim 1, wherein the end portion has a groove at an end portion facing the second fixed ring.

6. The joint apparatus of claim 5, wherein a point where the first contact portion and the first connection portion meet is disposed to correspond to the groove of the end portion, and a point where the second contact portion and the second connection portion meet is disposed to correspond to the groove of the end portion.

7. The joint apparatus of claim 1, wherein the end portion comprises:
a first part having a first width that is a largest width;
a second part having a second width and disposed in a direction toward the first fixed ring with respect to the first part; and
a third part having a third width and disposed in the direction toward the second fixed ring with respect to the first part,
wherein the first contact portion encompasses the end portion from the third part to the second part via the first part.

8. The joint apparatus of claim 1, further comprising a flexure connection portion that connects a point where the first contact portion and the first connection portion meet and a point where the second contact portion and the second connection portion meet, and supports the end portion.

9. The joint apparatus of claim 1, wherein the first flexure comprises a first extended portion connected to the first contact portion to be disposed at an opposite side to the first connection portion with respect to the first contact portion, and the second flexure comprises a second extended portion connected to the second contact portion to be disposed at an opposite side to the second connection portion with respect to the second contact portion.

10. The joint apparatus of claim 9, further comprising a stopper that protrudes from the bar and limits a position of the second fixed ring in the direction toward the first fixed ring as a portion of the stopper in the direction toward the second fixed ring contacts the first extended portion or the second extended portion.

11. The joint apparatus of claim 1, further comprising a stopper that protrudes from the bar and limits a position in the direction toward the first fixed ring of an end portion of the first flexure in the direction toward the first fixed ring, or a position in the direction toward the first fixed ring of an end portion of the second flexure in the direction toward the first fixed ring.

12. The joint apparatus of claim 1, further comprising:
a third fixed ring disposed at an opposite side to the first fixed ring with respect to the second fixed ring;
an additional extension portion comprising an additional bar extending from the second fixed ring in a direction toward the third fixed ring, and an additional end portion disposed at an end portion of the additional bar in the direction toward the third fixed ring;
a first additional flexure extending from the third fixed ring in the direction toward the second fixed ring and supporting the additional end portion; and
a second additional flexure extending from the third fixed ring in the direction toward the second fixed ring, supporting the additional end portion, and disposed at an opposite side to the first additional flexure with respect to the additional extension portion.

13. The joint apparatus of claim 1, further comprising:
a plate disposed at an opposite side to the first fixed ring with respect to the second fixed ring;
an additional extension portion comprising an additional bar extending from the second fixed ring in a direction toward the plate, and an additional end portion disposed at an end portion of the additional bar in a direction toward the plate;
a first additional flexure extending from the plate in the direction toward the second fixed ring and supporting the additional end portion; and
a second additional flexure extending from the plate in the direction toward the second fixed ring, supporting the additional end portion, and disposed at an opposite side to the first additional flexure with respect to the additional extension portion.

14. A joint apparatus comprising:
a first fixed ring;
a second fixed ring arranged spaced apart from the first fixed ring;
an extension portion comprising a bar extending from the first fixed ring in the direction toward the second fixed ring and an end portion disposed at an end portion of the bar in the direction toward the second fixed ring;
- a first flexure extending from the second fixed ring in the direction toward the first fixed ring;
- a second flexure extending from the second fixed ring in the direction toward the first fixed ring; and
- a flexure connection portion connecting an end portion of the first flexure in the direction toward the first fixed ring and an end portion of the second flexure in the direction toward the first fixed ring.

15. The joint apparatus of claim 14, wherein the flexure connection portion contacts the end portion.

16. The joint apparatus of claim 15, wherein the flexure connection portion encompasses the end portion.

17. The joint apparatus of claim 16, wherein the end portion comprises:
- a first part having a first width that is a largest width; and
- a second part having a second width and disposed in a direction toward the first fixed ring with respect to the first part, wherein the flexure connection portion encompasses the first part and the second part of the end portion.

18. The joint apparatus of claim 16, wherein the flexure connection portion has a concave shape in the direction toward the second fixed ring.

19. A joint apparatus comprising:
- a first fixed ring;
- a second fixed ring arranged spaced apart from the first fixed ring;
- an extension portion comprising a bar extending from the first fixed ring in the direction toward the second fixed ring and an end portion disposed at an end portion of the bar in the direction toward the second fixed ring; and
- a first flexure extending from the second fixed ring in the direction toward the first fixed ring, and comprising a first contact portion having a symmetric shape with respect to the bar and a portion contacting the end portion, and a first connection portion connecting the first contact portion and the second fixed ring.

20. The joint apparatus of claim 19, wherein the end portion comprises:
- a first part having a first width that is a largest width; and
- a second part having a second width and disposed in a direction toward the first fixed ring with respect to the first part, wherein the first contact portion encompasses the first part and the second part of the end portion.

* * * * *